United States Patent [19]

Anapliotis

[11] Patent Number: 4,809,689
[45] Date of Patent: Mar. 7, 1989

[54] DRILLING SYSTEM FOR INSERTION OF AN ENDOPROSTHESIS

[75] Inventor: Emmanuel Anapliotis, Berlin, Fed. Rep. of Germany

[73] Assignee: Mecron Medizinische Produkte GmbH, Berlin, Fed. Rep. of Germany

[21] Appl. No.: 923,926

[22] Filed: Oct. 28, 1986

[30] Foreign Application Priority Data

Oct. 28, 1985 [DE] Fed. Rep. of Germany ....... 3538654

[51] Int. Cl.$^4$ ................................................ A61F 5/04
[52] U.S. Cl. ............................ 128/92 VD; 128/92 VJ
[58] Field of Search ............ 128/92 V, 92 VD, 92 VJ

[56] References Cited

U.S. PATENT DOCUMENTS

| 4,187,559 | 2/1980 | Grell et al. | 128/92 VJ |
| 4,627,425 | 12/1986 | Reese | 128/92 VJ |
| 4,738,256 | 4/1988 | Freeman et al. | 128/92 VV |

FOREIGN PATENT DOCUMENTS 2356464  5/1975  Fed. Rep. of Germany .

*Primary Examiner*—C. Fred Rosenbaum
*Assistant Examiner*—Mark F. Colosimo
*Attorney, Agent, or Firm*—Spencer & Frank

[57] ABSTRACT

Drill system for an endoprosthesis including a drill gauge composed of: a straight, stem-like shaft and a guide element provided with a through bore for a drill, the guide element being connected with the stem-like shaft and the bore being oriented at an angle with respect to the shaft. The axes of shaft and bore essentially intersect and the guide element is fixed to the cylindrical, stem-like shaft.

9 Claims, 1 Drawing Sheet

DRILLING SYSTEM FOR INSERTION OF AN ENDOPROSTHESIS

BACKGROUND OF THE INVENTION

The present invention relates to a drilling system of the type defined in the preamble of claim 1 and to an associated prosthesis.

Cement-free prostheses are fixed in that a so-called press-fit situation is created. That means that the marrow region of the femur is shaped with the best possible precision so that a prosthesis of the correctly selected size for the respective femur can be hammered into the prepared marrow region with slight pressure. Adapting the marrow region to various prosthesis sizes is here possible only by means of a mechanical removal system. Removal with a conventional rasp, however, results in axial errors and, with great probability, produces a space which is too large in the proximal region, thus practically preprogramming the loosening of the prosthesis.

DE-AS No. 2,356,464 discloses a drill system as defined in the preamble of claim 1. The guide element which aligns the drill in an oblique position oriented toward the stem is displaceable in the associated drill gauge with respect to the stem-like shaft in the longitudinal direction of the latter. This displacement serves to completely cut out the prismatic region of the recess next to the cylindrical shaft so as to accommodate the corresponding part of the prosthesis. In its oblique position oriented toward the shaft, the cutter is brought toward the bone along a shaft which had previously been inserted into the bore until the cutter begins to widen the existing bore in the form of a triangular prism. If the obliquely directed cutter is advanced further, the prismatic region is excavated completely.

The drawback here is that the cutting takes place primarily along the sidelines of the cutter so that a force component (in the form of a bending moment) develops and bends the stem-like shaft, breaking it out of its guide in the bone. Moreover, the entire prismatic region must be removed by cutting, which in the course of surgery is a time-consuming process.

SUMMARY OF THE INVENTION

It is an object of the invention as defined in the characterizing portion of claim 1 to provide a drill system of the above-mentioned type which makes it possible to guide the cutter in an absolutely straight line with less exertion of force so that breaking out or faulty travel of the cutter need not be feared and thus the marrow region can be adapted with greater precision to the dimensions of a straight shaft prosthesis.

The invention is based on the realization that it is significantly easier to define the triangular, prismatic portion by an obliquely driven bore which is oriented toward the shaft and is delimited by an axially advanced bore and to break out the remaining (small) triangular portion with a few strokes of a chisel. This remaining region is formed by spongiosa which are not very strong and can be removed without difficulty in the small size regions remaining [after drilling]. If the stem-like shaft were to break out of its cylindrical preliminary bore in the region of the spongiosa, this would result right from the start in the prosthesis seat being loose, which must be avoided at any cost.

The cavity occupied by the straight-shaft prosthesis is produced by a first straight bore extending parallel to the bone and by a second converging bore oriented obliquely toward the first bore, with the bone substance region disposed between the two converging bores likewise essentially losing its support when the bores are made.

The distal marrow channel is here predrilled with a straight drill or cutter and the proximal area of the prosthesis is excavated by means of a further drill and with the aid of the drill gauge. This system offers far reaching security against the excavation of too much material and permits a good press fit seat for a prosthesis implanted without cement. Additionally, the system has the advantage that the resection plane can still be corrected with the aid of the drill gauge after the bore has been made and thus an accurate seat for the collar is realized.

In addition, the drill may also be provided with a through bore so as to be guided during drilling along a previously inserted guide lance so that the reliability with respect to perforation of the femur is additionally increased. It is important that with the use of the system according to the present invention, the period required for surgery is considerably shorted.

Thus, the system offers the following advantages.

Creation of a press fit situation assures the precisely fitting implantation and thus the primary fixation of a prosthesis implanted without cement.

Drilling with the guide lance is accurate and precise.

The surgical technique in the femur involves the following successive measures:

1. Start of drilling at the high trochanter with a Trocar.
2. Insertion of a guide lance into the marrow region.
3. Drilling, beginning with the smallest drill above the guide lance to the depth of the length of the prosthesis shaft, possibly controlled by a transducer, then drill with increasing cross section until the diameter of the drill gauge shaft is reached.
4. Resection of the head of the hip bone.
5. Insertion of the drill gauge.
6. Correction of the hip bone head osteotomy.
7. Drilling of the second bore along an Adam's arc until it contacts the drill gauge.
8. Excavation of the remaining spongiosa with a flat chisel, if necessary.
9. Hammering in the prosthesis to a precise fit.
10. Following up with an impactor.

Due to the fact that the round shaft and the bore are matched with one another in diameter by the bore guide element and the shaft is guided in a bore in the bone essentially without play, the bore having been produced by means of a drill which itself is guided essentially without play by the bore and, in particular, due to the fact that the diameter of the bore is equal to or slightly larger than the diameter of the shaft, both bores can be made with the same drill or cutter. Since both bores are advanced in the axial direction, no radially cutting cutter is required.

If, according to a further advantageous feature of the invention, the drill gauge is provided with a recess in the region in which a drill extending through the bore contact the drill gauge, with such recess delimiting the path of the drill in the direction toward the prosthesis by a transversely extending surface and the drill entering into this recess to its maximum cross section, the triangular, prismatic region at its side edges is completely free so that only the cover faces of this region need be loosened later by chiseling.

In another preferred embodiment, the guide element of the drill gauge containing the bore is provided with an abutment face at the side at which the axes of shaft and bore converge, with the area vector of this abutment face falling essentially into the plane defined by the center axes of the shaft and the drill. This plane is tangent on the reduced femur and corresponds to the "collar" of a prosthesis possibly later to be placed into the recess. It can be seen that, in its region to be inserted into the previously produced bore, is cylindrical or is configured so as to be introducible into a cylindrical body.

Advantageous features of the invention are defined in the remaining dependent claims and will be described in greater detail below in connection with a description of the preferred embodiment of the invention which is illustrated in the drawing.

DESCRIPTION OF THE PREFERRED EMBODIMENT

Figures 1, 2:
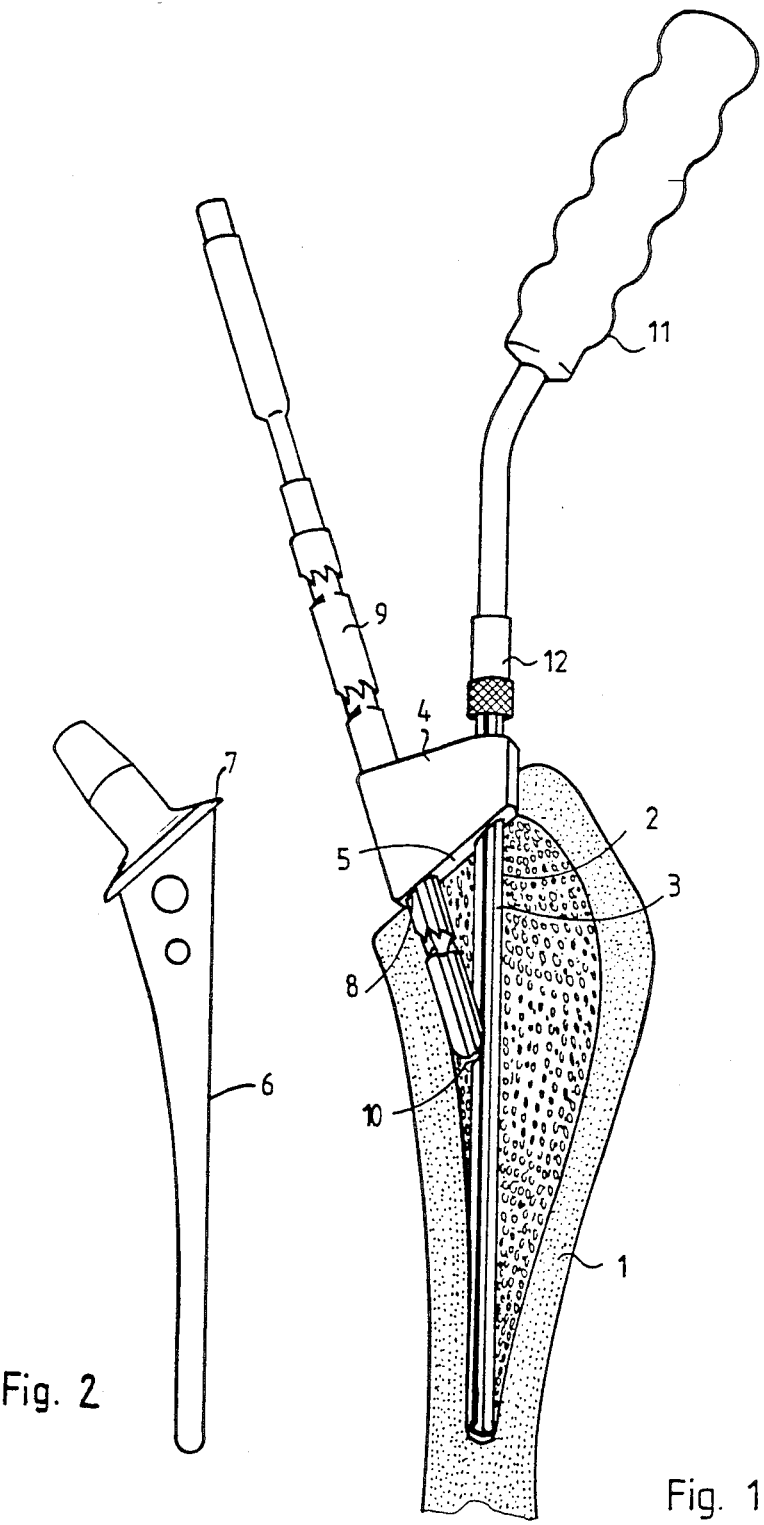
FIG. 1 depicts an embodiment of the drill system according to the invention comprising a drill gauge and a drill.
FIG. 2 depicts a prosthesis adapted to this drill system.

Initially a bore 2 has been made in femur 1 into which the shaft 3 of a drill gauge is introduced as part of the drill system according to the invention. It is here simultaneously possible to check the depth of the bore since, if the prosthesis is to be seated properly, a guide element 4, whose underside 5 is sloped at an angle corresponding to the collar of the prosthesis to be inserted into the recess, must rest on the bone. In the drawing figure, the outline of a straight-shaft prosthesis 6 with collar 7 is shown next to the drill gauge so that it can be easily seen that the interior of the bone, after having been excavated with the drill system according to the invention, substantially corresponds to the outline of the prosthesis. The (abutment) face thus formed on the underside 5 of the drill gauge corresponds to the slope of the underside of the collar of the associated, appropriately aligned prosthesis so that the seat of the drill gauge permits a good evaluation of the later seat of the prosthesis and it is possible, if necessary, to rework the bone material in time.

Guide element 4 has a bore 8 which is adapted to the cross section of a drill 9. This bore is arranged in such a manner that drill 9 is oriented toward shaft 3 and meets it in the region of a recess 10 which has such a configuration that it delimits the path of the drill in the direction toward the shaft. The diameter of bore 8 corresponds to the diameter of shaft 3 so that the drill, which has created the recess to accommodate the shaft, is itself guided in direction by the bore.

This recess 10 has an edge which constitutes the continuation of the part near the shaft, but traverses shaft 1 only in part and changes into a face oriented transversely to the axis of the continuation of the bore, forming an abutment for drill 9. Adjacent that side of guide element 4 where bore 8 and shaft 3 diverge, a handle 11 is provided following an angle to make it possible, on the one hand, to guide the drill gauge securely during insertion and removal and, on the other hand, to secure the drill gauge against inadvertent twisting before drill 9 inserted in bore 8 has engaged. The bend in the handle exposes the region of bore 8 for manipulation.

Handle 11 is connected with the shaft by means of a quick-release coupling which includes a knurled screw cap sleeve 12. Within screw sleeve 12, there is a plug-in connection which connects the separable parts in a manner protected against torques. In this way, the connection (not shown in detail in the drawing) permits the transfer of forces and moments in all directions.

If the two bores have been made in the femur region, it is assured that the prosthesis shaft of a press-fit prosthesis fits precisely and in the proper orientation.

Bone material possibly remaining between the two bores need be removed only roughly by means of a chisel since this material does not interfere with the guidance of the prosthesis but additionally improves its press-fit seat.

The guide element which, with respect to its lower abutment face, corresponds in its function to the collar of the future prosthesis, permits easy visual evaluation of the correct alignment of the drill gauge for insertion of the prosthesis and, if necessary, permits improved adaptation by additional removal of bone material.

The drill system according to the invention, composed of the described drill gauge and a drill or cutter having a matching cross section and a corresponding straight-shaft prosthesis as represented by outline 6. From the proximal to the distal end, the shaft of the prosthesis changes from an oval to a circular cross section. The outer edge is straight to collar 7 while the inner edge changes in a continuous curvature from the direction of the straight shaft of the drill gauge into the direction of the bore of its guide element. Correspondingly, the underside of collar 7 has an area orientation which corresponds to that of the underside of the drill gauge guide element.

The outer contour of the shaft of prosthesis 6 is thus essentially determined by the superposition of the shaft 3 of the drill gauge and a circular drill 9 inserted into bore 8 of guide element 4 and extending to the shaft and by the volume enclosed by the faces tangent on shaft and drill and disposed between them. The prosthesis has a collar 7 whose underside face corresponds in spatial orientation to face 5 at guide element 4 whose area vector falls essentially into the plane defined by the axes of the shaft and the bore.

The present invention is not limited in scope to the above-described, preferred embodiment. Rather, a number of variations are conceivable which utilize the illustrated solution also for basically different types of embodiments.

What is claimed is:

1. Drill system for the insertion of an endoprosthesis within a bone including a drill gauge comprising;
   a cylindrical, stem-like shaft having a recess, and
   a guide element provided with a through bore for accommodating a cutter, said guide element being fixed to said shaft, the bore being oriented at an angle with respect to said shaft and the axes of said shaft and said cutter within the bore essentially intersect;
   wherein said recess is located on said shaft where said shaft and said cutter intersect, said recess delimiting the path of said cutter in the direction toward said shaft by way of a transversely extending surface.

2. Drill system as defined in claim 1 wherein the cylindrical shaft (3) and the bore (8) of the guide element (4) are matched in diameter in such a manner that the shaft is guided essentially without play in an opening in the bone, said opening having been produced by means of said cutter which itself is guided by the bore essentially without play.

3. Drill system as defined in claim 1, wherein the diameter of the bore (8) is equal to or slightly larger than the diameter of the shaft (3).

4. Drill system as defined in claim 1, wherein, on the side of the guide element where the axes of said shaft and bore intersect, the drill gauge guide element (4) provided with the bore (8) has an abutment face, the surface of said abutment face falling essentially into the plane defined by the center axes of the shaft and the bore.

5. Drill system as defined in claim 1, wherein, the end of said shaft extending from said bone, is provided with a handle.

6. Drill system as defined in claim 5, wherein the end of the handle is bent, with the bend increasingly moving away from the axis of the bore.

7. Drill system as defined in claim 5, wherein the handle (11) is removable.

8. Drill system as defined in claim 5, wherein the handle (11) is connected with the shaft by means of a screw cap sleeve (12) and a quick-release coupling including a moment-locking plug-in connection.

9. Drill system as defined in claim 1, wherein the cross section of the cutter for excavating the bone material is adapted to the bore in the drill gauge guide element (4).

* * * * *